(12) United States Patent
Viola

(10) Patent No.: US 10,039,537 B2
(45) Date of Patent: Aug. 7, 2018

(54) MAGNETICALLY RETAINED INCISION CLOSURE DEVICES AND METHODS OF INCISION CLOSURE USING SAME

(71) Applicant: Covidien LP, Mansfield, MA (US)

(72) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 66 days.

(21) Appl. No.: 15/193,200

(22) Filed: Jun. 27, 2016

(65) Prior Publication Data

US 2016/0302781 A1    Oct. 20, 2016

Related U.S. Application Data

(62) Division of application No. 12/721,651, filed on Mar. 11, 2010, now Pat. No. 9,402,605.

(60) Provisional application No. 61/169,927, filed on Apr. 16, 2009.

(51) Int. Cl.
*A61B 17/08* (2006.01)
*A61B 17/00* (2006.01)
*A61B 17/064* (2006.01)

(52) U.S. Cl.
CPC ........ *A61B 17/0057* (2013.01); *A61B 17/085* (2013.01); *A61B 2017/00606* (2013.01); *A61B 2017/00615* (2013.01); *A61B 2017/00623* (2013.01); *A61B 2017/00637* (2013.01); *A61B 2017/00818* (2013.01); *A61B 2017/00862* (2013.01); *A61B 2017/00867* (2013.01); *A61B 2017/00876* (2013.01); *A61B 2017/0641* (2013.01)

(58) Field of Classification Search
CPC ...... A61B 17/0057; A61B 2017/00575; A61B 2017/00606; A61B 2017/00615; A61B 2017/00637; A61B 17/11; A61B 2017/1103; A61B 2017/1107; A61B 17/1114; A61B 2017/1135; A61B 2017/1139; A61B 2017/1132
See application file for complete search history.

(56) References Cited

U.S. PATENT DOCUMENTS

| | | | |
|---|---|---|---|
| 3,986,493 | A | 10/1976 | Hendren, III |
| 4,338,937 | A | 7/1982 | Lerman |
| 4,917,114 | A | 4/1990 | Green et al. |
| 5,336,233 | A | 8/1994 | Chen |
| 5,342,393 | A | 8/1994 | Stack |
| 5,346,501 | A | 9/1994 | Regula et al. |
| 6,068,637 | A | 5/2000 | Popov et al. |
| 6,352,543 | B1 | 3/2002 | Cole |
| 6,503,259 | B2 | 1/2003 | Huxel et al. |

(Continued)

FOREIGN PATENT DOCUMENTS

| | | |
|---|---|---|
| EP | 0517488 A1 | 12/1992 |
| EP | 0595094 A2 | 5/1994 |

(Continued)

OTHER PUBLICATIONS

European Search Report for EP 10 25 0786 date of completion is Aug. 11, 2010 (3 pages).

*Primary Examiner* — Jonathan Miles

(57) ABSTRACT

An incision closure device includes an elongated handle portion including a distal end, a first connector detachably affixed to the distal end of the handle portion, and a second connector adapted to be axially moveable along the handle portion, wherein the first and second connectors are magnetically attracted to one another.

16 Claims, 13 Drawing Sheets

(56) References Cited

U.S. PATENT DOCUMENTS

| | | |
|---|---|---|
| 6,632,229 B1 | 10/2003 | Yamanouchi |
| 6,719,768 B1 | 4/2004 | Cole et al. |
| 8,162,974 B2 | 4/2012 | Eskuri et al. |
| 9,402,605 B2 | 8/2016 | Viola |
| 2002/0143347 A1 | 10/2002 | Cole et al. |
| 2003/0055455 A1 | 3/2003 | Yang et al. |
| 2004/0215214 A1 | 10/2004 | Crews et al. |
| 2005/0021059 A1 | 1/2005 | Cole et al. |
| 2006/0271107 A1 | 11/2006 | Harrison et al. |
| 2007/0010834 A1 | 1/2007 | Sharkawy et al. |
| 2008/0114384 A1 | 5/2008 | Chang et al. |
| 2008/0200934 A1 | 8/2008 | Fox |
| 2009/0048618 A1 | 2/2009 | Harrison et al. |
| 2009/0312789 A1 | 12/2009 | Kassab et al. |

FOREIGN PATENT DOCUMENTS

| | | |
|---|---|---|
| EP | 1493391 A1 | 1/2005 |
| FR | 2760627 A1 | 9/1998 |
| WO | 8100668 A1 | 3/1981 |
| WO | 2004105693 A2 | 12/2004 |
| WO | 2007016261 A2 | 2/2007 |
| WO | 2008061024 A2 | 5/2008 |
| WO | 2008150905 A1 | 12/2008 |
| WO | 2009029228 A2 | 3/2009 |

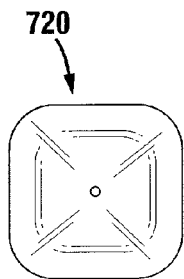 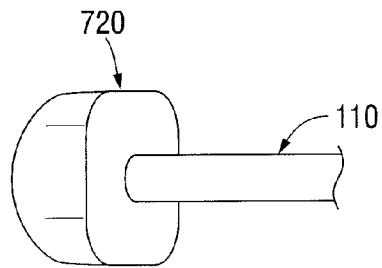
FIG. 7A　　　　　FIG. 7B
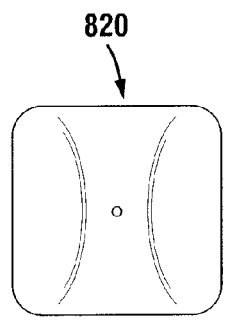 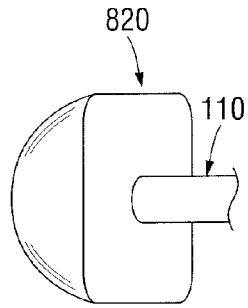 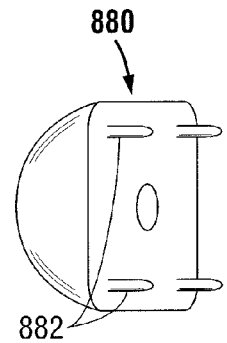
FIG. 8A　　　　FIG. 8B　　　　FIG. 8C
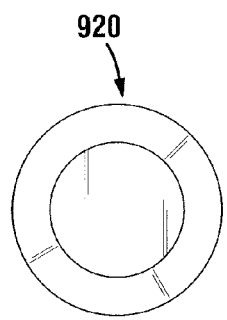 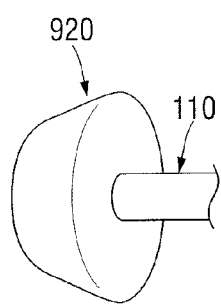 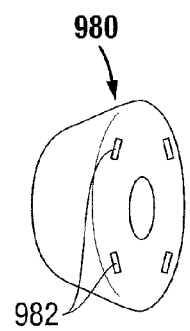
FIG. 9A　　　　FIG. 9B　　　　FIG. 9C

MAGNETICALLY RETAINED INCISION CLOSURE DEVICES AND METHODS OF INCISION CLOSURE USING SAME

CROSS-REFERENCE TO RELATED APPLICATION

This application is a divisional of U.S. patent application Ser. No. 12/721,651 filed Mar. 11, 2010, which claims benefit of and priority to U.S. Provisional Application No. 61/169,927 filed Apr. 16, 2009, and the disclosures of each of the above-identified applications are hereby incorporated by reference in their entirety.

BACKGROUND

1. Technical Field

The present disclosure relates to surgical devices for closing surgical access sites or other wounds and, more particularly, to surgical devices and methods suitable for use in the closure of gastric or colonic incisions.

2. Discussion of Related Art

Endoscopic or minimally invasive surgical approaches utilize small incisions. Surgical instruments of various kinds are guided through these small incisions. Typically, when performing tissue approximation during endoscopic surgery, the incision is closed with sutures, surgical staples, or clips.

Natural Orifice Translumenal Endoscopic Surgery (NOTES) represents a new phase of minimally invasive surgery. The secure closure of the gastrotomy or colotomy site in transluminal surgery is difficult. NOTES has the potential to eliminate complications associated with traditional surgery, such as postoperative abdominal wall pain, wound-related and pulmonary complications, hernias, adhesions, and possibly impaired immune function. Challenges to the advancement and clinical acceptance of NOTES include the need for secure enterotomy closure.

The secure closure of gastric or colonic incisions in endoscopy and transluminal endoscopy is important. A need exists for surgical devices suitable for closure of wounds and incisions such as gastric or colonic incisions.

SUMMARY

The present disclosure relates to an incision closure device including an elongated handle portion including a distal end, a first connector detachably affixed to the distal end of the handle portion, and a second connector adapted to be axially moveable along the handle portion. The first and second connectors are magnetically attracted to one another.

The present disclosure relates to an incision closure device including a first connector capable of producing a magnetic field, a second connector capable of producing a magnetic field, and a handle portion including a first section having a first diameter and a second section disposed proximal to the first section. The second section has a second diameter that is larger than the first diameter. The first connector is configured to be detachably affixed to a distal end of the first section of the handle portion.

The present disclosure also relates to a method of incision closure that includes the initial step of positioning an incision closure device relative to a surgical access site. The incision closure device includes a first connector, a second connector, and a deployment member. The first connector is detachably mounted on the distal end of the deployment member, and the second connector is slideably mounted on the deployment member proximal to the first connector. The first and second connectors are magnetically attracted to one another. The method also includes the steps of causing the first connector to pass through an incision at the surgical access site by moving the deployment member a first distance in a first direction, placing the second connector in contact with tissue by moving the deployment member a second distance in the first direction, and placing the first connector in contact with tissue by moving the deployment member a third distance in a second direction opposite to the first direction.

BRIEF DESCRIPTION OF THE DRAWINGS

Objects and features of the presently disclosed incision closure devices and methods of incision closure using the same will become apparent to those of ordinary skill in the art when descriptions of various embodiments thereof are read with reference to the accompanying drawings, of which:

FIGS. 7A and 7B are frontal and side perspective views respectively of a first connector of an incision closure device according to an embodiment of the present disclosure;

FIGS. 8A and 8B are frontal and side perspective views respectively of a first connector of an incision closure device according to another embodiment of the present disclosure;

FIG. 8C is a side perspective view of the first connector illustrated FIGS. 8A and 8B shown with pin elements according to an embodiment of the present disclosure;

FIGS. 9A and 9B are frontal and side perspective views respectively of a first connector of an incision closure device according to yet another embodiment of the present disclosure;

FIG. 9C is a side perspective view of the first connector illustrated FIGS. 9A and 8B shown with apertures according to an embodiment of the present disclosure;

DESCRIPTION OF EMBODIMENTS

Figure 1:
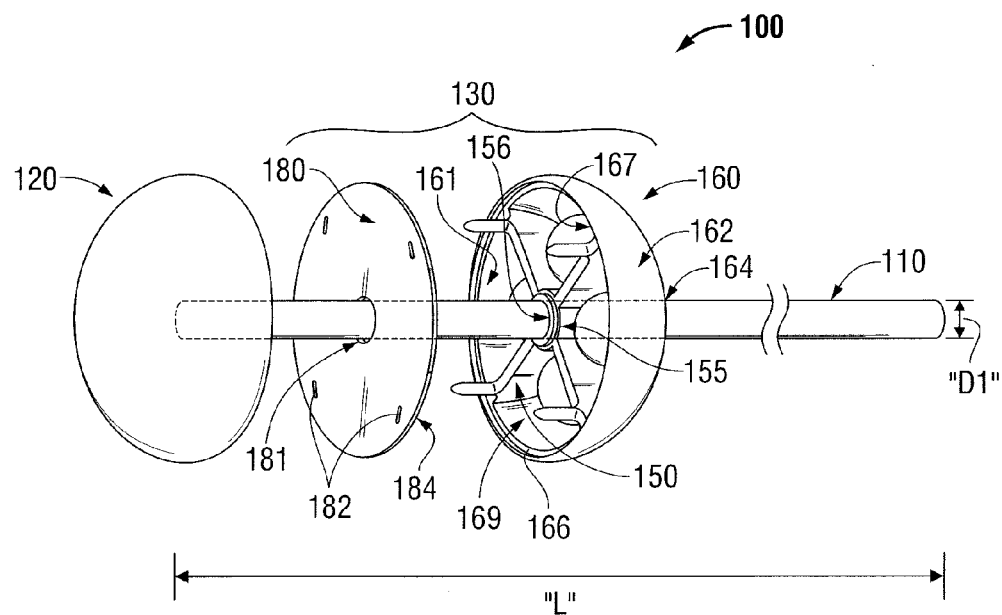
FIG. 1 is a perspective view of an incision closure device according to an embodiment of the present disclosure.

Hereinafter, embodiments of the presently disclosed incision closure device and methods of incision closure using the same will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the phrase "magnetic material" and the term "magnet" generally refer to any material capable of producing a magnetic field. Although it may be convenient for the purposes of this disclosure to refer to a magnet as having distinct north and south magnetic poles, it is to be understood that this is merely a way of referring to the two different ends of a magnet.

In various embodiments, the presently disclosed incision closure device includes first and second connectors, which are configured to be magnetically attracted to one another, and a delivery and/or deployment member (also referred to herein as a "handle portion") adapted to axially align the first and second connectors to facilitate closure of incisions, e.g., gastric or colonic incisions, or other wounds. Although various methods described hereinbelow are targeted toward closure of gastric or colonic incisions, it is to be understood that methods of incision closure may be used with other procedures.

Figure 2:
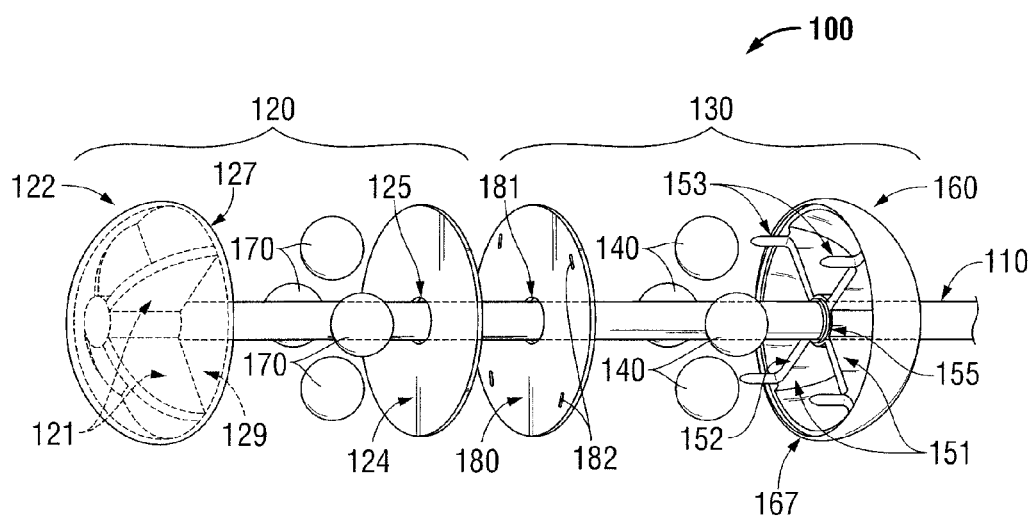
FIG. 2 is an exploded view of the incision closure device illustrated in FIG. 1 according to an embodiment of the present disclosure.

FIGS. 1 and 2 show an incision closure device 100 according to an embodiment of the present disclosure that includes an elongated handle portion 110, a first connector 120 detachably affixed to the distal end of the handle portion 110, and a second connector 130 adapted to be axially moveable along the handle portion 110. The shape and size of the first connector 120 and the second connector 130 may be varied from the configurations depicted in FIGS. 1 and 2.

Handle portion 110 may be formed of any suitable material, e.g., metal, such as aluminum, or plastic, such as polyethylene, polycarbonate, or polyvinyl chloride (PVC), or combination thereof. Handle portion 110 may be formed as a substantially solid member having a cylindrical or rod-like shape having a length "L", and may have a uniform or substantially uniform diameter "D1" throughout the entire length "L". In embodiments, the handle portion 110 is formed entirely of a substantially rigid material, such as, for example, metal, synthetic or compound materials. In embodiments, the handle portion 110 may include a flexible, malleable or shape memory material. The shape and size of the handle portion 110 may be varied from the configuration depicted in FIGS. 1 and 2. According to embodiments of the present disclosure, the handle portion 110, or portions thereof, may have a curved shape, e.g., to facilitate desirable placement and positioning of the first and second connectors 120, 130 within a body cavity or hollow organ (e.g., within or by way of the intestines or the gastrointestinal tract).

First connector 120 according to various embodiments includes a first portion 122 and a second portion 124. First portion 122 is generally formed as a hollow body having an open end with a peripheral edge 127, and may be formed of any suitable material, such as metal or biocompatible plastic or combination thereof. First portion 122 may include material that is resistant to gastric acid and/or other bodily fluids. In embodiments, the first portion 122 has a substantially half-spherical or dome-like shape defining an interior chamber 129 configured to receive one or more magnets 170 therein, and may include one or more separating arms or walls 121.

Separating arms 121 may be configured to partition the interior chamber 129 into a plurality of compartments configured to receive one or more magnets 170 therein. For example, as shown in FIG. 2, the interior chamber 129 of the first portion 122 may be configured to contain four magnets 170, individually disposed in separate compartments defined by four separating arms 121. In various embodiments, the separating arms 121 may be integrally formed with the first portion 122, e.g., injection molded, or separately formed and then joined to the first portion 122 by a wide variety of adhesive and bonding techniques including soldering. Separating arms 121, or portions thereof, may be formed of non-magnetic materials.

Although the first connector 120 illustrated in FIGS. 1 and 2 has a substantially half-spherical first portion 122, it is to be understood that the first connector 120 may be formed in various sizes and shapes. In some cases, the particular procedure and/or the size of the incision to be closed may dictate a particular first connector configuration in order to achieve a desired surgical outcome. Some examples of first connector configurations are shown generally as 720, 820, 880, 920, and 980 are shown in FIGS. 7A, 7B, 8A, 8B, 8C, 9A, 9B and 9C.

Second portion 124 of the first connector 120 generally includes an opening 125 formed therein configured to receive the handle portion 110 therethrough. In some embodiments, the second portion 124 of the first connector 120 is formed substantially entirely of a suitable magnetic material. Second portion 124 may include any material capable of producing a magnetic field. Examples of magnetic materials that may be used to form the second portion 124 include, but are not limited to, NdFeB (Neodymium Iron Boron), AlNiCo (Aluminum Nickel Cobalt), SmCo (Samarium Cobalt), strontium ferrite, and barium ferrite. In some embodiments, the second portion 124, or portions thereof, includes one or more non-magnetic materials. Second portion 124 may include any combination of magnetic and non-magnetic materials. In some embodiments, the second portion 124 may include paramagnetic materials, e.g., magnesium, molybdenum, lithium and/or tantalum.

Second connector 130 of the presently disclosed incision closure device 100 includes a housing 160 configured to be axially moveable along the handle 110. In embodiments, the housing 160 has a substantially half-spherical or dome-like shape defining an interior chamber 169 extending from a peripheral edge 167. Interior chamber 169 according to various embodiments is configured to receive one or more magnets 140 therein. Second connector 130 may also include a cover 180 and a support member 150 adapted to be slideably moveable along the handle portion 110. In embodiments, the one or more magnets 140 each have a substantially spherical shape. Cover 180 generally includes an opening 181 formed therein configured to receive the handle portion 110 therethrough. Cover 180 may also include one or more apertures 182 formed therethrough.

Housing 160 generally includes an inner surface 161 and an outer surface 162, and may be formed to accommodate various number, sizes and shapes of magnets 140. Housing 160 includes an opening 164 formed therein configured to receive the handle portion 110 therethrough. Housing 160 may be formed of any suitable material, such as metal, biocompatible plastic, or combination thereof. In embodiments, the housing 160 includes a recessed wall portion 166 spaced from the peripheral edge 167 of the housing 160 and configured to receive a peripheral edge area 184 of the cover 180 therein. Recessed wall portion 166 may be provided with an adhesive film (not shown) or other material for bonding or otherwise securing the cover 180 to the housing 160. In embodiments where the housing 160 and the cover 180 are formed of thermoplastic, the peripheral edge area 184 of the cover 180 and the recessed wall portion 166 of the housing 160 may be heat welded together.

Support member 150 according to various embodiments includes a collar portion 155 defining an opening 156, which is advantageously dimensioned to receive the handle portion 110 therethrough. In embodiments, the support member 150 includes one or more separating arms or walls 151 extending generally radially outward from the collar portion 155 toward the housing 160. In an embodiment, four, substantially equal length separating arms 151 are each connected to a separate respective portion of the housing 160. For example, each separating arm 151 may be connected to a separate respective portion of the inner surface 161 of the housing 160. As shown in FIG. 1, the interior chamber 169 of the housing 160 may be configured to contain four magnets 140, e.g., individually disposed in separate compartments defined by four separating arms 151. Separating arms 151, or portions thereof, may be formed of non-magnetic materials.

Second connector 130 may be provided with one or more pin elements 153 configured to extend distally beyond the peripheral edge 167 of the housing 160 toward the first connector 120. Pin elements 153 are generally arranged to align with the apertures 182 in the cover 180, and may extend substantially perpendicular to a distal surface 152 of the separating arms 151. Pin elements 153 may extend substantially parallel to a longitudinal axis of the handle portion 110. In embodiments, the pin elements 153 are attached to the separating arms 151. Pin elements 153 are advantageously shaped and dimensioned to penetrate into body tissue. In an embodiment of the presently disclosed incision closure device, a first connector (e.g., 980 shown in FIG. 9C) includes apertures configured to receive at least a portion of the pin elements 153. Pin elements 153 may be formed of any suitable material, e.g., metal or plastic. The thickness of the cover 180 may be varied depending on various factors, such as, for example, the length of the pin elements 153, materials used to form the cover 180 and the pin elements 153, tissue, characteristics, and/or incision size or other incision characteristics. It is to be understood that the number, position, length, and shape of the pin elements 153 may be varied from the configurations depicted in FIGS. 1 and 2. Although four pin elements 153 are illustrated in FIGS. 1 and 2, it is be understood that the second connector 130 may include various number of pin elements.

Support member 150 may be formed of any suitable material. In some embodiments, the support member 150 may be formed of a substantially rigid material, such as metal (e.g., stainless steel) or plastic (e.g., polyvinyl chloride (PVC), polystyrenes, polyurethanes, thermoplastic elastomers, and acrylics).

Procedures for the delivery and deployment of the first and second connectors 120 and 130 of the presently disclosed incision closure device 100 are described later in this disclosure with reference to FIGS. 12A through 12G.

Figure 3:
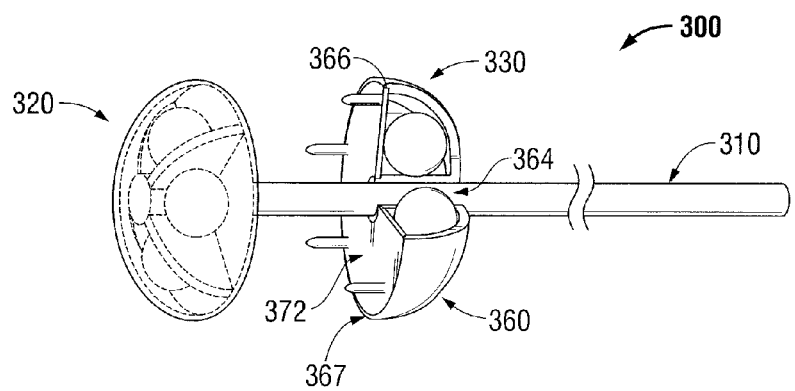
FIG. 3 is a perspective view in partial relief of an incision closure device according to another embodiment of the present disclosure.
Figure 4:
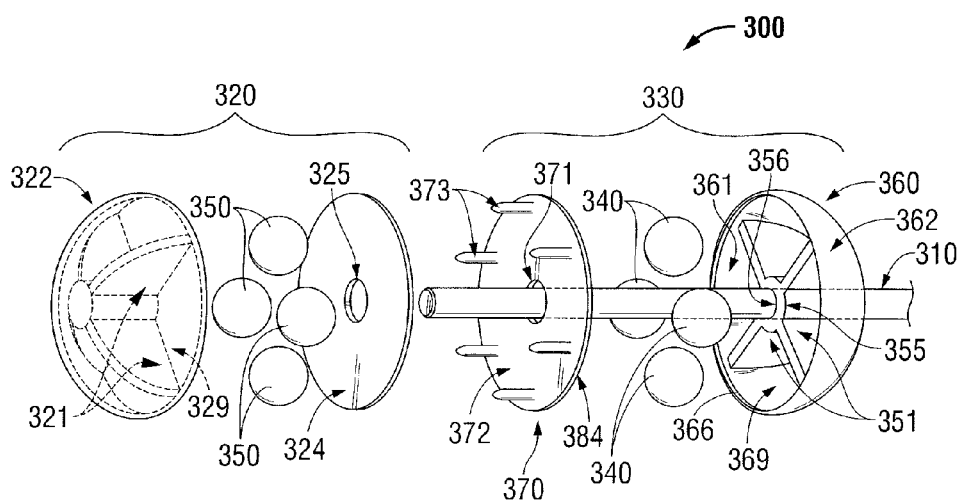
FIG. 4 is an exploded view of the incision closure device illustrated in FIG. 3 according to an embodiment of the present disclosure.

FIGS. 3 and 4 show an incision closure device 300 according to an embodiment of the present disclosure that includes an elongated handle portion 310, a first connector 320 detachably affixed to the distal end of the handle portion 310, and a second connector 330 adapted to be axially moveable along the handle portion 310. Handle portion 310 may be formed of any suitable material, such as metal or plastic or combination thereof. Handle portion 310 is similar to the handle portion 110 shown in FIGS. 1 and 2 and further description thereof is omitted in the interests of brevity.

First connector 320 includes a first portion 322 and a second portion 324. First portion 322 is generally formed as a hollow body having an open end with a peripheral edge 367, and may be formed of any suitable material, such as metal or biocompatible plastic or combination thereof. In an embodiment of the presently disclosed incision closure device 300, the first connector 320 is substantially the same as the first connector 120 illustrated in FIGS. 1 and 2. For example, in one instance, the first and second portions 322, 324 of the first connector 320 are substantially the same, respectively, as the first and second portions 122, 124 shown in FIGS. 1 and 2.

In embodiments, the first portion 322 has a substantially half-spherical or dome-like shape defining an interior chamber 329 configured to receive one or more magnets (e.g., four magnets 350 shown in FIG. 4) therein, and may include one or more separating arms or walls 321. Separating arms 321 may be configured to partition the interior chamber 329 into a plurality of compartments configured to receive one or more magnets 350 therein. Second portion 324 of the first connector 320 generally includes an opening 325 formed therein configured to receive the handle portion 310 therethrough. Second portion 324 may be formed from magnetic materials, non-magnetic materials, or combinations thereof.

Second connector 330 according to various embodiments includes an axially moveable housing 360 defining an interior chamber 369 configured to receive one or more magnets (e.g., four magnets 340 shown in FIG. 4) therein, and a wall portion or cover 370 adapted to be slideably moveable along the handle portion 310. In an embodiment of the presently disclosed incision closure device 300, the magnets 340 are substantially the same as the magnets 140 shown in FIGS. 1 and 2.

In embodiments, the housing 360 has a substantially half-spherical or dome-like shape. Housing 360 may be formed of any suitable material, such as metal or biocompatible plastic or combination thereof. Housing 360 includes an opening 364 formed therein configured to receive the handle portion 110 therethrough. In embodiments, the housing 360 includes a recessed wall portion 366 spaced from a peripheral edge 367 of the housing 360 and configured to receive a peripheral edge area 384 of the wall portion 370 therein. Recessed wall portion 366 may be provided with an adhesive film (not shown) or other material for bonding or otherwise securing the cover wall portion 370 to the housing 360.

Wall portion 370 generally includes an opening 371 formed therein configured to receive the handle portion 310 therethrough. In some embodiments, the wall portion 370 includes at least three pin elements 373 extending forwardly toward the first connector 320. Pin elements 373 may extend substantially perpendicular to a distal surface 372 of the wall portion 370. Pin elements 373 are advantageously shaped and dimensioned to penetrate into body tissue. Although six pin elements 373 are illustrated in FIG. 4, it is be understood that the wall portion 370 may include various number of pin elements and/or pin shapes.

Figure 5:
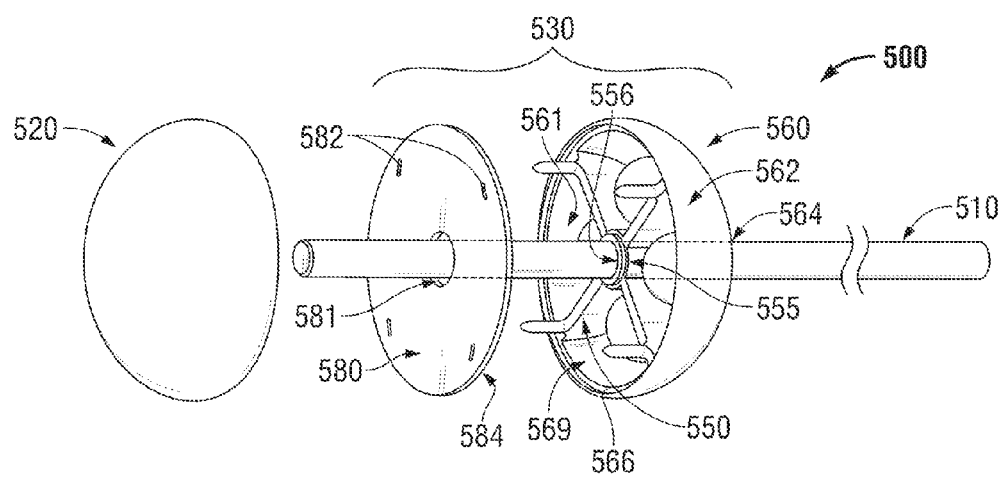
FIG. 5 is a perspective view of an incision closure device according to another embodiment of the present disclosure.
Figure 6:
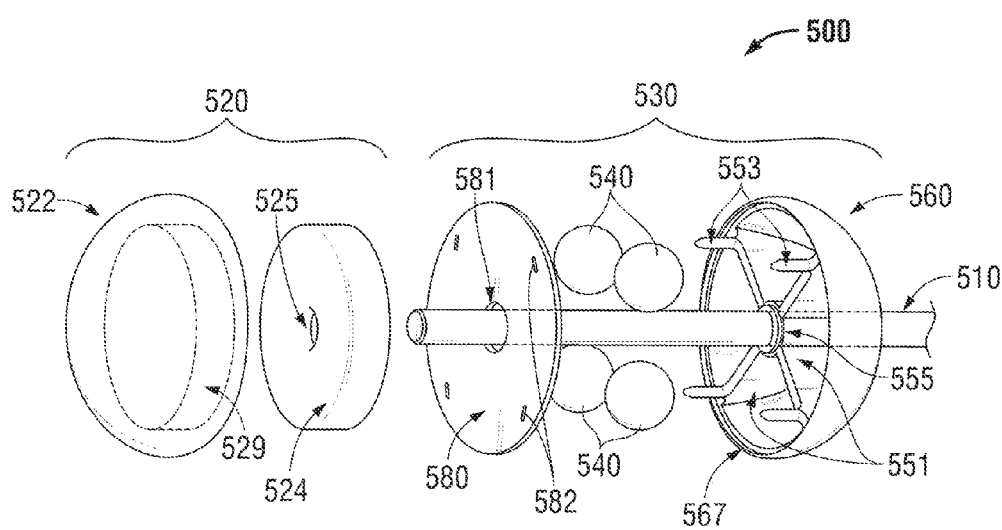
FIG. 6 is an exploded view of the incision closure device illustrated in FIG. 5 according to an embodiment of the present disclosure.

FIGS. 5 and 6 show an incision closure device 500 according to an embodiment of the present disclosure that includes an elongated handle portion 510, a first connector 520 detachably affixed to the distal end of the handle portion 510, a second connector 530 adapted to be axially moveable along the handle portion 510. Handle portion 510 may be formed of any suitable material, such as metal or plastic or combination thereof. Handle portion 510 is similar to the handle portion 110 shown in FIGS. 1 and 2 and further description thereof is omitted in the interests of brevity.

The first connector 520 includes a first portion 522 and a second portion 524. In embodiments, the second portion 524 of the first connector 520 is formed substantially entirely of a magnetic material. In embodiments, the second portion 524 includes one or more non-magnetic materials. For example, non-magnetic materials may be used to partition the second portion 524 into two or more separate regions of magnetic material. Second portion 524 generally includes an opening 525 formed therein configured to receive the handle portion 510 therethrough. First portion 522 of the first connector 520 may be advantageously shaped and dimensioned to house the second portion 524 therein. For example, as shown in FIG. 6, the first portion 522 may define a cavity or chamber 529 configured to receive the second portion 524 therein. Chamber 529, or portions thereof, may be provided with an adhesive film (not shown) or other material for bonding the second portion 524 to the first portion 522.

Second connector 530 includes an axially moveable housing 560 defining an interior chamber 569 configured to receive one or more magnets 540 therein, a cover 580, and a support member 550 adapted to be slideably moveable along the handle portion 510. Cover 580 is arranged between the housing 560 and the second portion 524 of the first connector 520. Housing 560 generally includes an inner surface 561 and an outer surface 562, and may be formed to accommodate various number, sizes and shapes of magnets 540. In an embodiment of the presently disclosed incision closure 500, the housing 560 is substantially the same as the housing 160 shown in FIGS. 1 and 2. For example, in one instance, the support member 550 of the second connector 530 is substantially the same as the support member 150 shown in FIGS. 1 and 2.

Support member 550 according to various embodiments includes a collar portion 555 defining an opening 556 configured to receive the handle portion 110 therethrough, and may include one or more separating arms or walls 551 extending generally radially outward from the collar portion 555 toward the housing 560. In embodiments, a plurality of substantially equal length separating arms 551 are each connected to a separate respective portion of the inner surface 561 of the housing 560.

Second connector 130 may be provided with one or more pin elements 553 configured to extend distally beyond the peripheral edge 567 of the housing 560 toward the first connector 520. In embodiments, the pin elements 553 are coupled to the separating arms 151.

Cover 580 includes an opening 581 formed therein that is advantageously dimensioned to receive the handle portion 510. Cover 580 may also include one or more apertures 582 configured to receive the pin elements 553 therethrough. In embodiments, the pin elements 553 and the apertures 582 may be designed and configured to be interlocking. Although the distal and proximal surfaces of the cover 580 shown in FIGS. 5 and 6 are generally flat, it is to be understood that the distal and proximal surfaces of cover 580 according to various embodiments may be curved or may include a combination of flat, sloped or curved portions. The thickness of the cover 580 may be varied depending on various factors, such as, for example, the length of the pin elements 553, materials used to form the cover 580 and the pin elements 553, tissue, characteristics, and/or incision size or other incision characteristics.

In embodiments, the housing 560 has a substantially half-spherical or dome-like shape. Housing 560 may be formed of any suitable material, such as metal or biocompatible plastic or combination thereof. Housing 560 includes an opening 564 formed therein configured to receive the handle portion 110 therethrough. In embodiments, the housing 560 includes a recessed wall portion 566 configured to receive a peripheral edge area 584 of the cover 580 therein. Recessed wall portion 566 may be provided with an adhesive film (not shown) or other material for bonding the cover 580 to the housing 560.

The shape and size of the first connector 520 and the second connector 530 may be varied from the configurations depicted in FIGS. 5 and 6. For example, in lieu of the first connector 520, the presently disclosed incision closure device may be configured with one of the first connector embodiments (e.g., 720, 820, 880, 920, or 980) shown in FIGS. 7A through 9C. As shown in FIG. 8C, the presently disclosed first connector may include one or more pin elements 882. Pin elements 882 are similar the pin elements 373 shown in FIG. 4 and further description thereof is omitted in the interests of brevity. As shown in FIG. 9C, the presently disclosed first connector may include one or more apertures 982, which may be configured to receive pin elements (e.g., 553 shown in FIG. 6) therein. According to various embodiments, the presently disclosed first connector may include one or more pin elements and/or apertures, and the presently disclosed second connector may include one or more pin elements and/or apertures.

Figure 10:
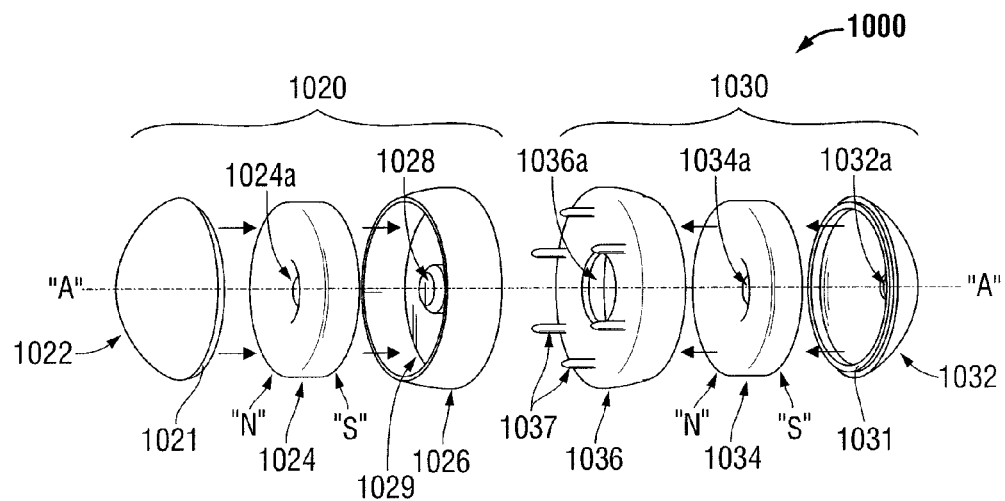
FIG. 10 is an exploded view of first and second connectors of an incision closure device according to an embodiment of the present disclosure.
Figure 11:
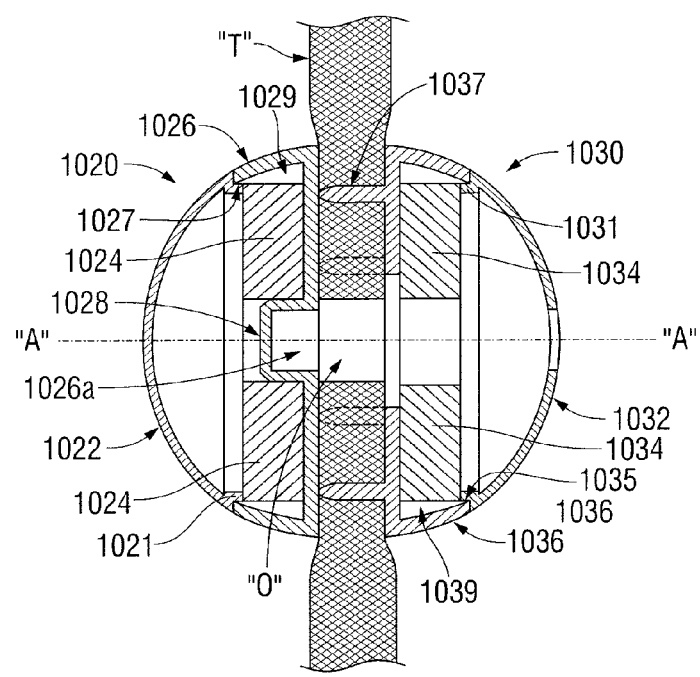
FIG. 11 is a cross-sectional view of the first and second connector assemblies illustrated in FIG. 10 shown in a deployed configuration according to an embodiment of the present disclosure.

FIGS. 10 and 11 show an incision closure device 1000 according to an embodiment of the present disclosure that includes a first connector 1020 configured to be detachably affixed to the distal end of a handle portion (e.g., 710 shown in FIG. 15) and a second connector 1030 adapted to be axially moveable along the handle portion. In FIGS. 10 and 11, the first and second connector assemblies 1020, 1030 are shown axially aligned with one another along a central axis "A". Procedures that may be suitable for the delivery and/or deployment of the first and second connectors 1020 and 1030 of the presently disclosed incision closure device 1000 are described later in this disclosure with reference to FIGS. 12A through 12G and FIGS. 16A through 16E.

FIG. 10 is an exploded view of the first connector assembly 1020 and the second connector assembly 1030 of the presently disclosed incision closure device 1000. As shown in FIG. 10, the first connector assembly 1020 may include a first cap 1022, a first member 1024 including an opening 1024a defined therein, and a first housing portion 1026 defining an interior chamber 1029 configured to receive the first member 1024 therein.

First housing portion 1026 according to various embodiments includes a connector portion 1028 extending into the chamber 1029. In embodiments, the connector portion 1028 defines a recess (e.g., 1026a shown in FIG. 11) configured to receive a distal end of a handle portion (e.g., 710 shown in FIG. 15) therein. As cooperatively shown in FIGS. 10 and 11, the connector portion 1028 of the housing portion 1026 may be configured to fit within the opening 1024a of the first member 1024 when the first member 1024 and the housing portion 1026 are coupled together.

In embodiments, the second connector assembly 1030 includes a second cap 1032, a second member 1034 including an opening 1034a defined therein, and a second housing portion 1036 defining an interior chamber 1039 (shown in FIG. 11) configured to receive the second member 1034 therein.

First cap 1022 of the first connector 1020 and the second cap 1032 of the second connector assembly 1030 may be formed of any suitable material, such as metal or biocompatible plastic or combination thereof. Second cap 1032 generally includes an opening 1032a formed therein configured to receive a handle portion (not shown) therethrough. As cooperatively shown in FIGS. 10 and 11, the first cap 1022 includes a flange portion 1021 configured to engage an inner peripheral edge 1027 of the first housing portion 1026, and the second cap 1032 includes a flange portion 1031 configured to engage an inner peripheral edge 1035 of the second housing portion 1036. The shape and size of the first cap 1022 and the second cap 1032 may be varied from the configurations depicted in FIGS. 10 and 11.

In embodiments, each of the first and second members 1024, 1034 are magnets. It is to be understood that the first and second members 1024, 1034 may include any material capable of producing a magnetic field. Examples of magnetic materials that may be used to form the first and second members 1024, 1034 include, but are not limited to, NdFeB (Neodymium Iron Boron), AlNiCo (Aluminum Nickel Cobalt) SmCo (Samarium Cobalt), strontium ferrite and barium ferrite.

First and second members 1024, 1034 illustrated in FIG. 10 each have a generally annular body including a distal surface, which may be regarded as corresponding to its north pole "N", a proximal surface, which may be regarded as corresponding to its south pole "S", and an outer diameter wall. In embodiments, the outer diameter wall of the first member 1024 is advantageously dimensioned to fit within the interior chamber 1029 of the first housing portion 1026 of the first connector assembly 1020. In embodiments, the outer diameter wall of the second member 1034 is advantageously dimensioned to fit within the interior chamber 1039 of the second housing portion 1036 of the second connector assembly 1030.

Second housing portion 1036 may include at least three pin elements 1037 extending forwardly toward the first connector 1020. Pin elements 1037 may extend substantially perpendicular to a surface of the second housing portion 1036. Pin elements 1037 are advantageously shaped and dimensioned to penetrate into body tissue. Although six pin elements 1037 are illustrated in FIG. 10, it is be understood that the second housing portion 1036 may include various number of pin elements, such as three pin elements to establish a plane.

FIG. 11 is a cross-sectional view of the first and second connector assemblies illustrated in FIG. 10 shown in a deployed configuration, according to an embodiment of the present disclosure. The magnetic attraction between opposite poles of the axially-aligned first and second connector assemblies 1020, 1030 facilitates the secure closure of the incision "O". For example, in one instance, the magnetic attraction between the proximal end (e.g., "S" shown in FIG. 10) of the first magnetic member 1024 and the distal end (e.g., "N" shown in FIG. 10) of the second magnetic member 1034 maintains the first and second connector assemblies 1020, 1030 in intimate contact with the tissue "T" near or adjacent to the site of a surgical incision "O", forming a secure closure of the incision.

The amount of compression force exerted by the axially-aligned first and second connector assemblies 1020, 1030 on the tissue "T" will depend on various factors including the magnetic materials used to form the first and second members 1024, 1032, the materials (magnetic and/or non-magnetic) used to form the first housing portion 1026 of the first connector assembly 1020, the materials (magnetic and/or non-magnetic) used to form the second housing portion 1036 of the second connector assembly 1030, and/or tissue characteristics, e.g., cellular density.

FIGS. 12A through 12G illustrate a method of incision closure using the presently disclosed incision closure device 100 shown in FIGS. 1 and 2). It is to be understood, however, that other incision closure device embodiments may also be used (e.g., 300, 500 and 1000 shown in FIGS. 3, 5 and 10, respectively). As shown in FIGS. 12C through 12F, an outer sleeve member 105, configured to slideably engage the handle portion 110, may be used to exert a biasing force against the second connector 130, e.g., to move the second connector 130 along the handle portion 110 toward the surgical access site "S". In embodiments, the outer sleeve member 105 includes a hollow cylindrical body having an inner surface with an inner diameter, which is larger than the outer diameter of the handle portion 110. Outer sleeve member 105 may include a grip portion (not shown) configured for grasping by the surgeon.

Figure 12A:
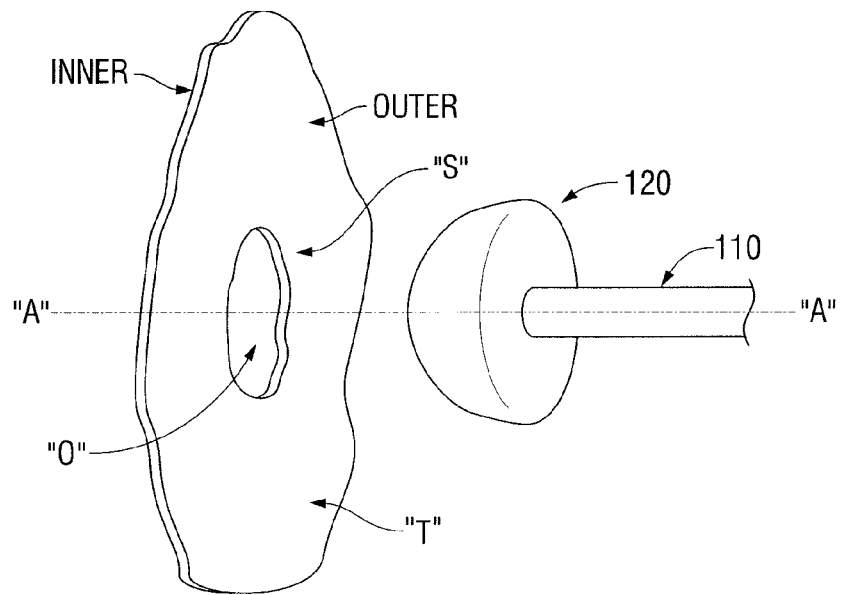
FIGS. 12A through 12G illustrate a method of incision closure using the incision closure device shown in FIGS. 1 and 2 according to an embodiment of the present disclosure.

Referring to FIG. 12A, the first connector 120 at the distal end of the handle portion 110 is delivered to a surgical access site "S", e.g., near an outer or proximal surface of tissue "T", and the surgeon aligns the first connector 120 and/or the handle portion 110 with the incision or opening "O" in the tissue "T". For example, the surgeon may position the incision closure device 100 relative to the surgical access site "S" such that a longitudinal axis "A" of the handle portion 110 is centrally aligned with the opening "O" in the tissue "T".

Figure 12B:
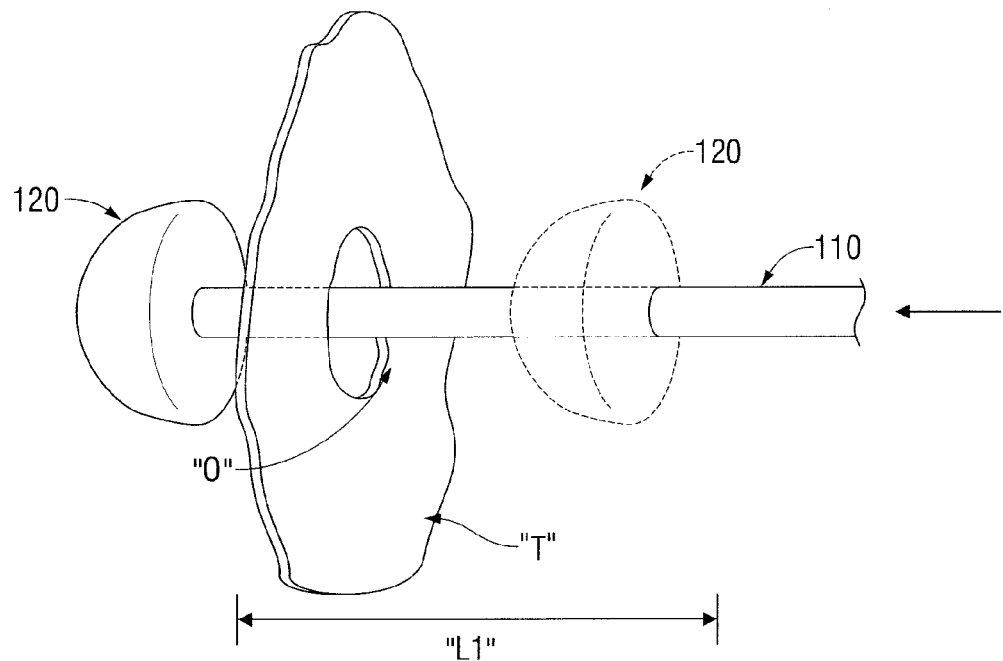

After the first connector 120 is aligned with the opening, the surgeon moves the handle portion 110 a first length "L1" in a first direction (also referred to herein as a distal or forward direction), as indicated by the left arrow in FIG. 12B, so that the first connector 120 is moved through the opening "O" to a position near the inner or distal surface of tissue "T", e.g., close to the opening "O".

Figure 12C:
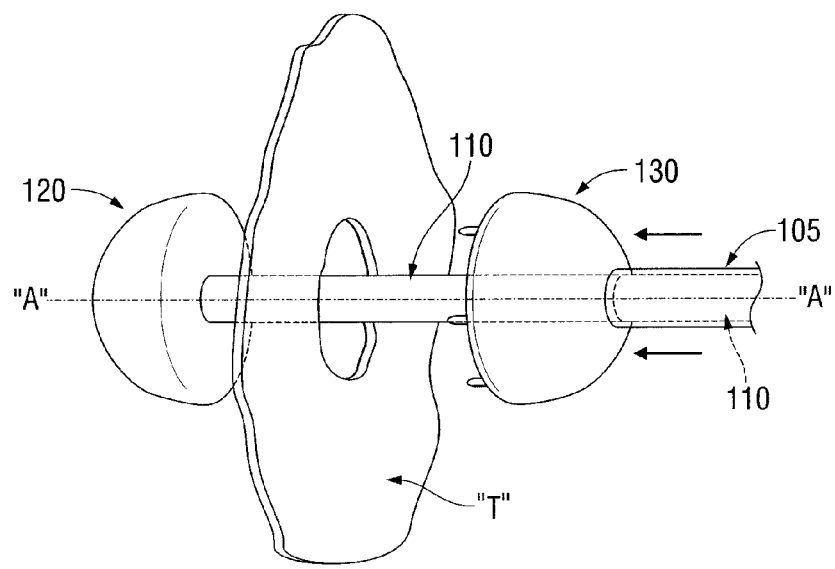
Figure 12D:
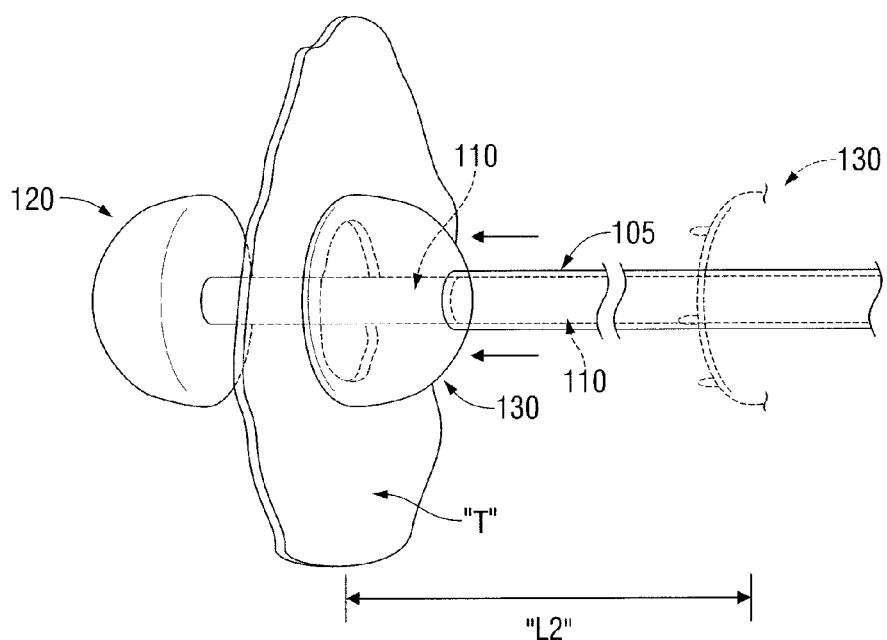

As shown in FIGS. 12C and 12D, the surgeon may use the presently disclosed outer sleeve member 105 to move the second connector 130 in a forward direction, as indicated by the left arrows in FIGS. 12C and 12D, along the handle portion 110. As shown in FIG. 12D, the second connector 130 may be moved a length "L2" along the handle portion 110 to place the second connector 130 in contact with the proximal surface of the tissue "T".

Figure 12E:
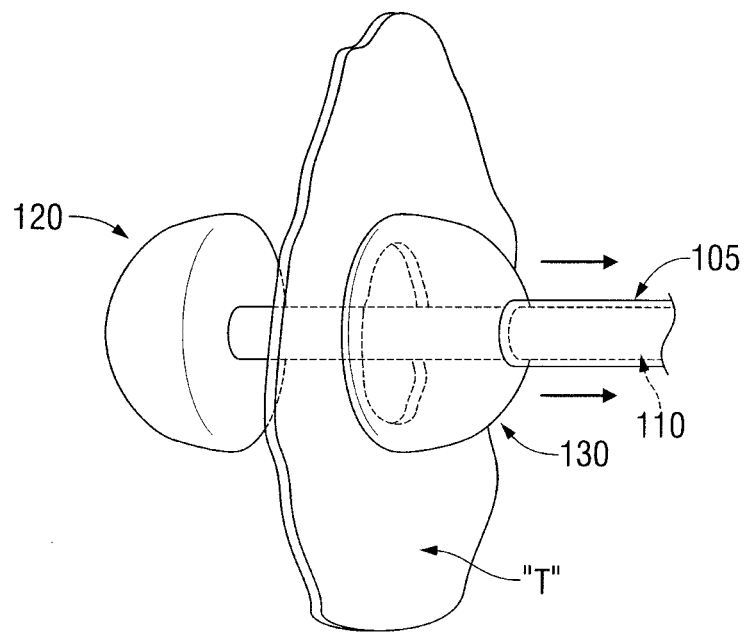
Figure 12F:
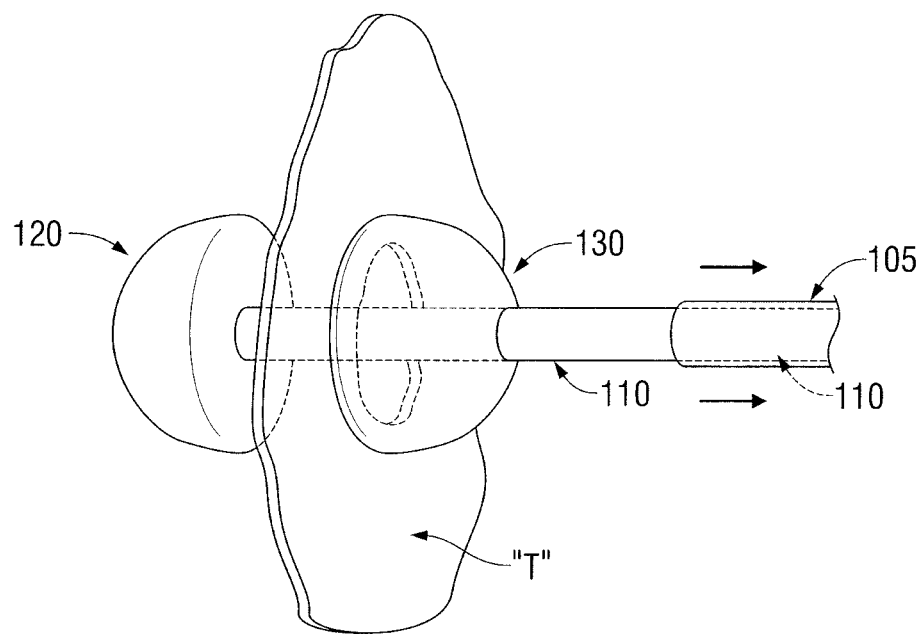

After the second connector 130 is placed in contact with the proximal surface of the tissue "T", the outer sleeve member 105 may be moved in a second direction (also referred to herein as a proximal direction), as indicated by the right arrows in FIGS. 12E and 12F, to partially, or entirely, remove the outer sleeve member 105 from the handle portion 110.

Figure 12G:
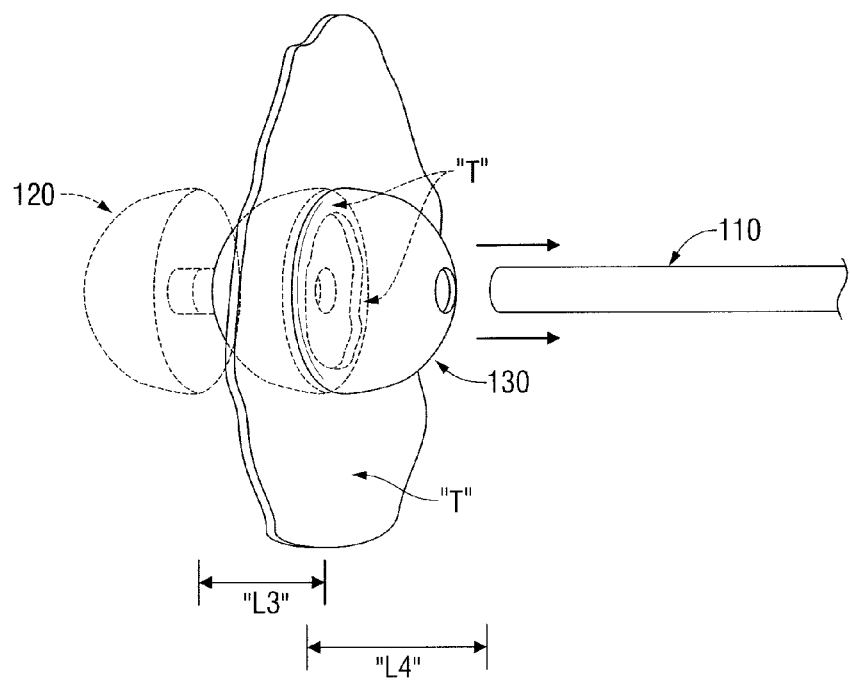

While the second connector 130 is in contact with the proximal surface of tissue "T", the handle portion 110 is moved in the second direction, as indicated by the right arrows in FIG. 12G, to move the first connector 120 toward the distal surface of the tissue "T". In embodiments, by moving the handle portion 110 a third distance "L3" in the second direction, the first connector 120 is brought into contact with the distal surface of the tissue "T". Magnetic attraction between the presently disclosed first and second connectors 120, 130 maintains the incision closure device 100 in intimate contact with the tissue "T".

Figure 13:
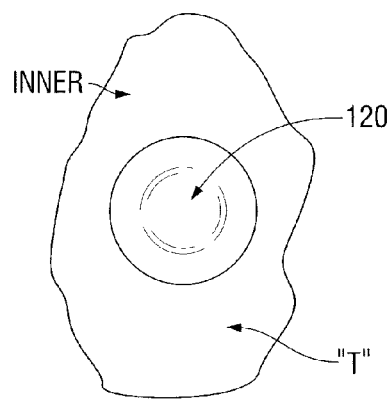
FIGS. 13 and 14 are perspective views of the first and second connector assemblies illustrated in FIGS. 1 and 2 shown in a deployed configuration, according to an embodiment of the present disclosure.
Figure 14:
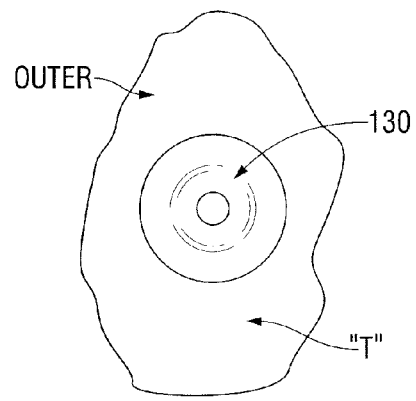

While the axially-aligned first and second connectors 120, 130 are in contact with the tissue "T", the handle portion 110 is retracted free of the first and second connectors 120, 130 by moving the handle portion 110 a fourth distance "L4" in the second direction as shown in FIG. 12G. FIGS. 13 and 14 show the deployed first and second connectors 120, 130 of the presently disclosed incision closure device 100.

Figure 15:
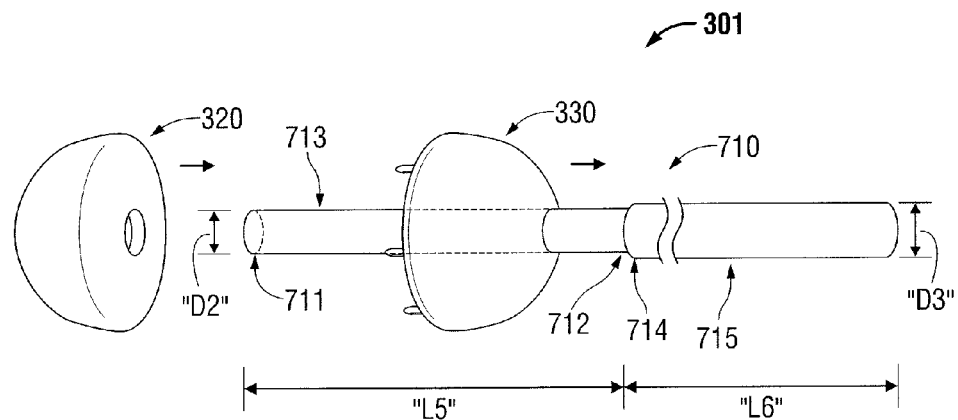
FIG. 15 is a perspective view of the first and second connector assemblies illustrated in FIGS. 3 and 4 shown with another embodiment of a deployment member in accordance with the present disclosure.

According to another embodiment of the present disclosure, an incision closure device, shown generally as 301 in FIG. 15, includes the first connector 320 and the second connector 330 illustrated in FIGS. 3 and 4, and a delivery and/or deployment member 710 (also referred to herein as a "handle portion"). In embodiments, the handle portion 710 may be formed of metal, synthetic or compound materials. The shape and size of the handle portion 710 may be varied from the configuration depicted in FIG. 15.

In embodiments, the handle portion 710 includes a first section 713 having a distal end 711, and a second section 715 having a distal end 714 disposed adjacent a proximal end 712 of the first section 713. As shown in FIG. 15, the first section 713 has a first length "L5" and a first diameter "D2", and the second section 715 has a second length "L6" and a second diameter "D3", where "D3">"D2". In embodiments, the first diameter "D2" of the handle portion 710 may be the same as the diameter "D1" of the handle portion 110 shown in FIG. 1.

FIGS. 16A through 16E illustrate a method of incision closure using the presently disclosed incision closure device 301 shown in FIG. 15. In embodiments, in an initial step, the second connector 330 is axially positioned on the first section 713 of the handle portion 710 adjacent the distal end 714 of the second section 715 of the handle portion 710, and the second connector 330 is detachably affixed to the distal end 711 of the first section 713, as cooperatively shown in FIGS. 15 and 16A.

Figure 16A:
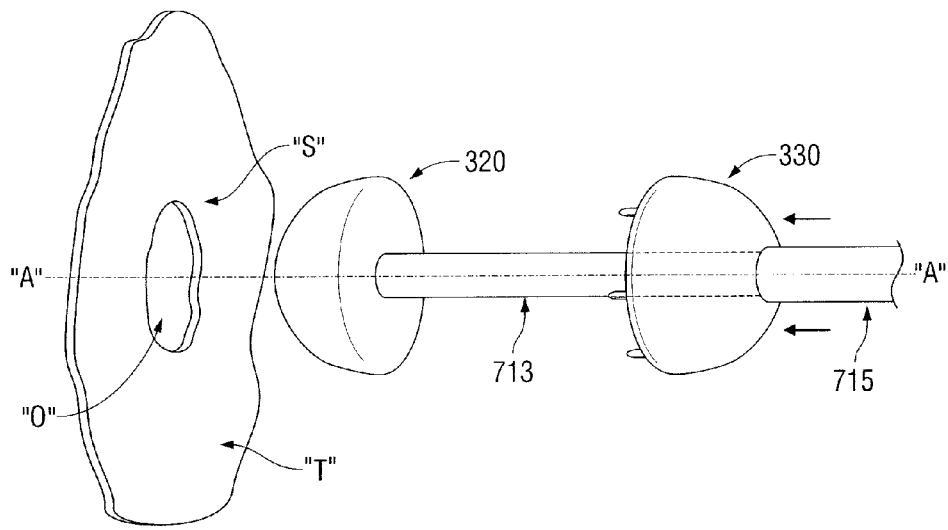
FIGS. 16A through 16E illustrate a method of incision closure using the incision closure device shown in FIG. 15 according to an embodiment of the present disclosure.
Figure 16B:
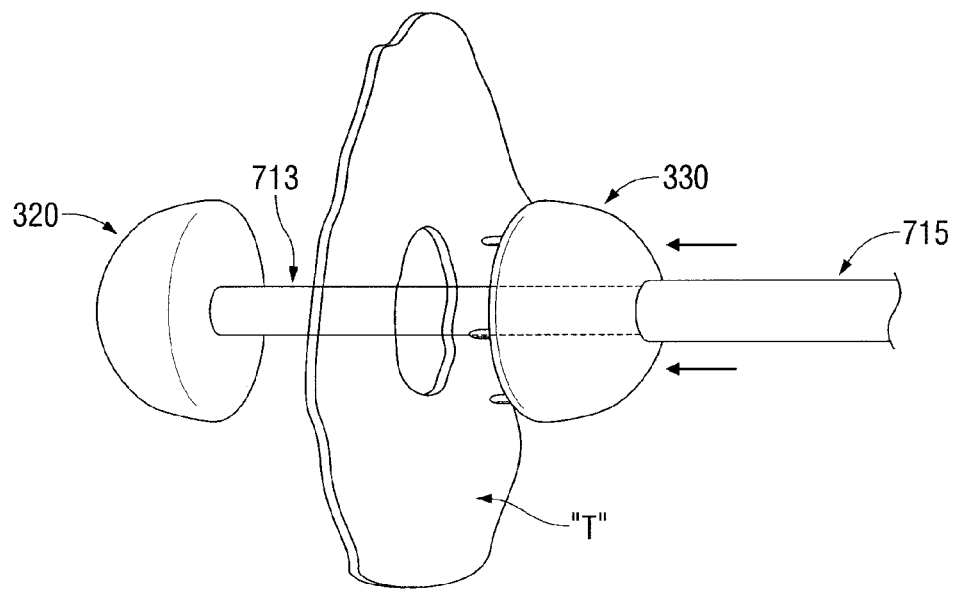

Referring to FIG. 16A, the first connector 120 at the distal end 713a of the handle portion 110 is delivered to a surgical access site "S", e.g., near an outer or proximal surface of tissue "T", and the surgeon aligns the first connector 120 and/or the handle portion 110 with the incision or opening "O" in the tissue "T". For example, the surgeon may position the incision closure device 100 relative to the surgical access site "S" such that a longitudinal axis "A" of the handle portion 110 is centrally aligned with the opening "O" in the tissue "T".

After the first connector 120 is aligned with the opening, the surgeon moves the handle portion 110 a first length "L1" in a first direction (also referred to herein as a distal or forward direction), as indicated by the left arrow in FIG. 12B, so that the first connector 120 is moved through the opening "O" to a position near the inner or distal surface of tissue "T", e.g., in close proximity to the opening "O".

Hereinafter, a method of incision closure, in accordance with the present disclosure, is described with reference to FIG. 17. It is to be understood that the steps of the method provided herein may be performed in combination and in a different order than presented herein without departing from the scope of the disclosure.

Figure 17:
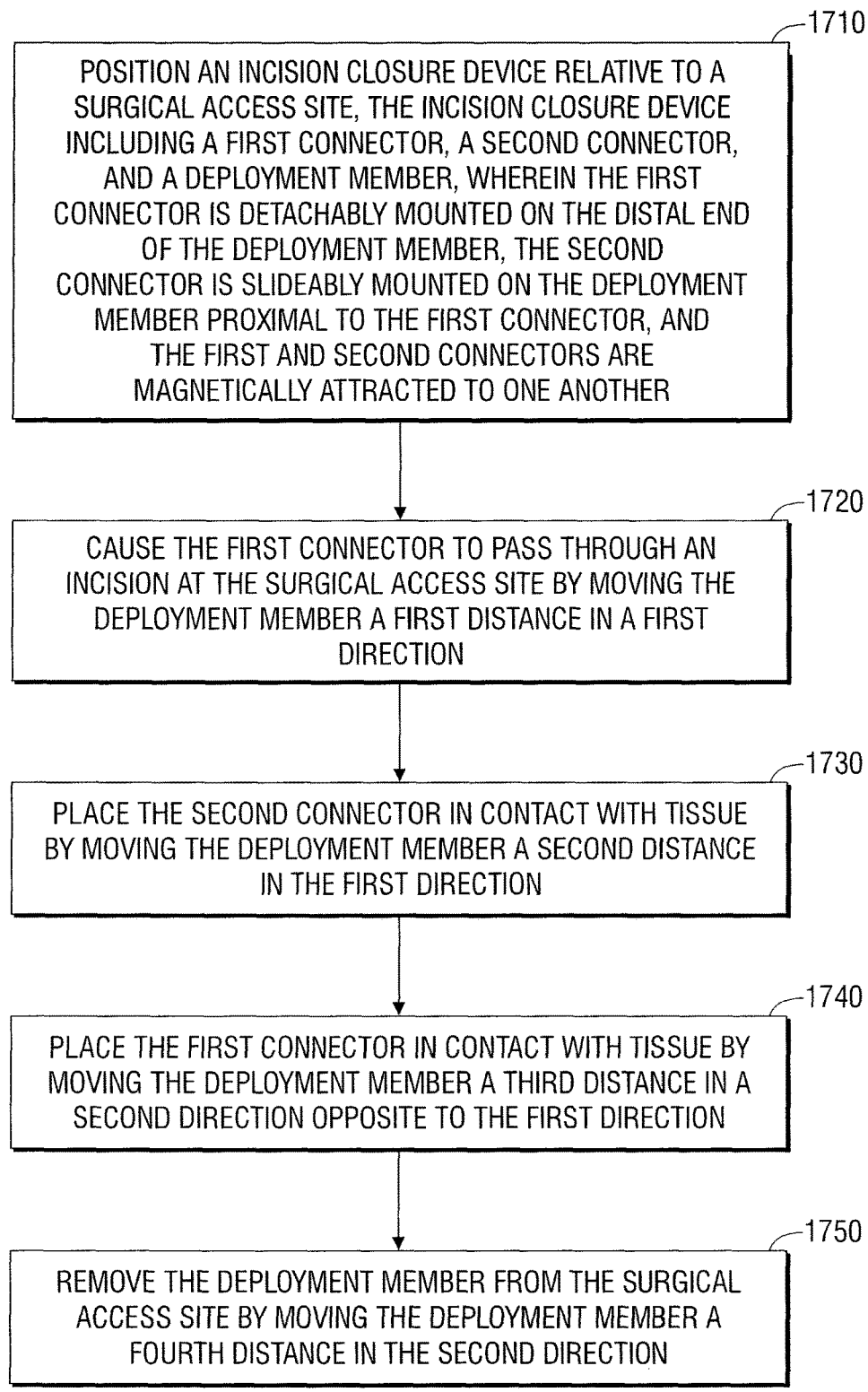
FIG. 17 is a flowchart illustrating a method of incision closure according to an embodiment of the present disclosure.

FIG. 17 is a flowchart illustrating a method of incision closure according to an embodiment of the present disclosure. In step 1710, an incision closure device (e.g., 301 shown in FIG. 15) is positioned relative to a surgical access site (e.g., "S" shown in FIG. 16A). The incision closure device includes a first connector (e.g., 320 shown in FIG. 15), a second connector (e.g., 330 shown in FIG. 15) and a deployment member (e.g., 710 shown in FIG. 15). The first connector is detachably mounted on the distal end (e.g., 713a shown in FIG. 15) of the deployment member. The second connector is slideably mounted on the deployment member proximal to the first connector. The first and second connectors are magnetically attracted to one another.

In step 1720, the deployment member is moved a first distance in a first direction (e.g., as indicated by the left arrows in FIG. 16A), causing the first connector to pass through an incision (e.g., "O" shown in FIG. 16A) at the surgical access site (e.g., "S" shown in FIG. 16A).

Figure 16C:
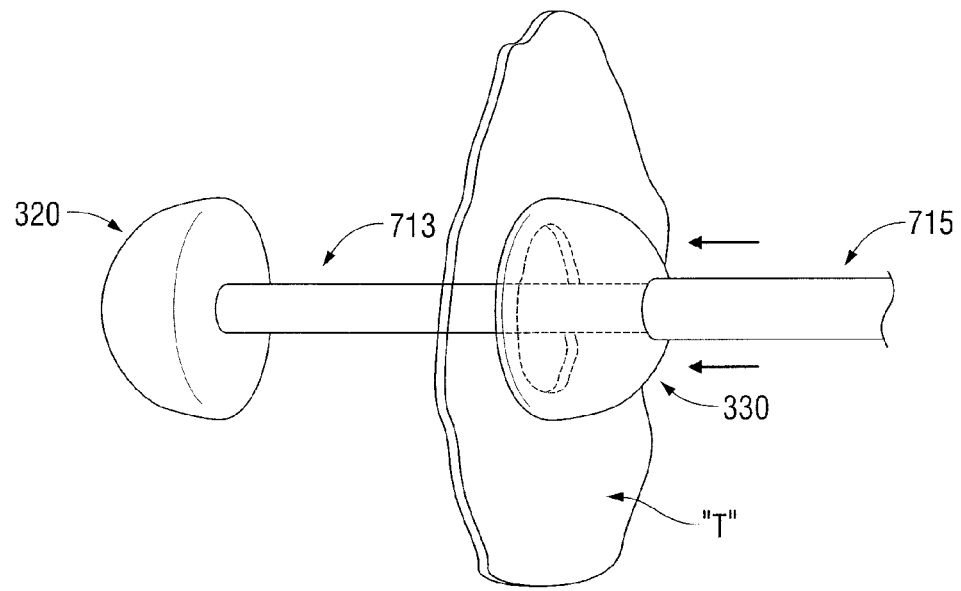
Figure 16D:
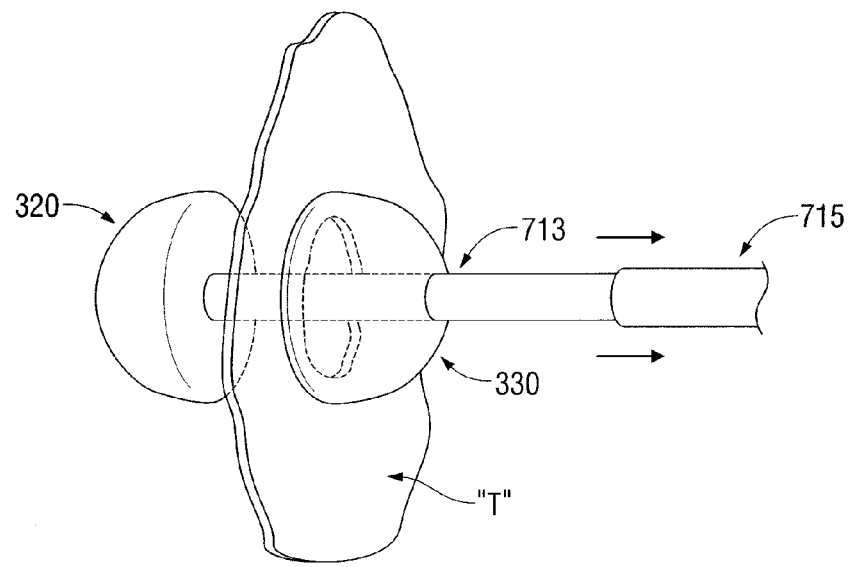
Figure 16E:
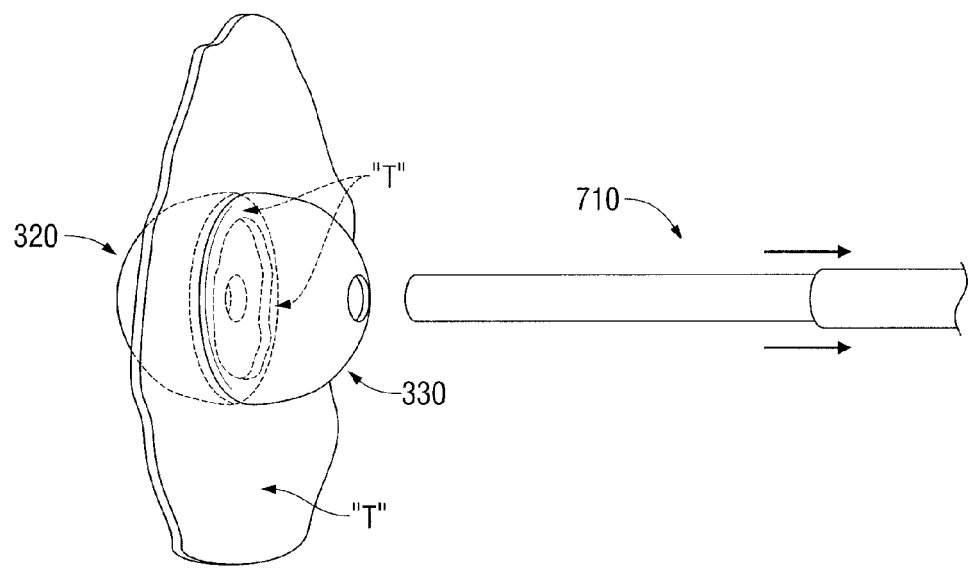

In step 1730, the deployment member is moved a second distance in the first direction, placing the second connector in contact with tissue (e.g., "T" shown in FIG. 16C).

In step 1740, the deployment member is moved a third distance in a second direction (e.g., as indicated by the right arrows in FIG. 16D) that is opposite to the first direction, placing the first connector in contact with tissue. In embodiments, the magnetic attraction between the magnets (e.g., 170 shown in FIG. 2) of the first connector and the magnets (e.g., 140 shown in FIG. 2) of the second connector maintains the first and second connectors in intimate contact with tissue (e.g., "T" shown in FIG. 16E) at the surgical access site, forming a secure incision closure.

In step 1750, the deployment member is moved a fourth distance in the second direction, removing the deployment member from the surgical access site.

In various embodiments, the presently disclosed incision closure device includes first and second connectors, which are configured to be magnetically attracted to one another, and a delivery and/or deployment member (also referred to herein as a "handle portion") adapted to axially align the first and second connectors to facilitate closure of incisions or other wounds. In various embodiments of the presently disclosed incision closure device and methods of incision closure using the same, the magnetic attraction between the axially-aligned first and second connectors may help to facilitate the formation of a reliable, secure incision closure.

The presently disclosed first connector and/or the second connector may be provided with one or more pin elements configured to penetrate tissue, which may help to facilitate the formation of a reliable, secure incision closure. In embodiments, the first connector and/or the second connector may include one or more apertures configured to receive the pin elements therein, which may enhance the reliability of the incision closure, e.g., by inhibiting lateral movement of the first connector relative to the second connector.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of closing a surgical incision, the method comprising:
    positioning an incision closure device relative to a surgical access site, the incision closure device including a first connector, a second connector, and a deployment member, wherein the first connector is detachably mounted on a distal portion of the deployment member and the second connector is operably coupled to the deployment member proximal to the first connector, wherein the first and second connectors are magnetically attracted to one another;
    causing the first connector to pass through an incision in tissue at the surgical access site by moving the deployment member a first distance in a first direction;
    placing the second connector in contact with tissue by moving the deployment member a second distance in the first direction;
    placing the first connector in contact with tissue by moving the deployment member a third distance in a second direction opposite to the first direction; and
    maintaining the first connector in a spaced relation with the second connector at a distance equal to a length of at least one pin element operably coupled to at least one of the first connector or the second connector.

2. The method of closing a surgical incision of claim 1, further comprising:
    detaching the first connector from the deployment member; and
    removing the deployment member from the surgical access site by moving the deployment member a fourth distance in the second direction.

3. The method of closing a surgical incision of claim 1, wherein placing the second connector in contact with tissue includes penetrating tissue via at least one pin element operably coupled to the second connector.

4. The method of closing a surgical incision of claim 1, wherein the length extends to a distal-most end of the at least one pin element.

5. The method of closing a surgical incision of claim 1, wherein positioning the incision closure device includes the second connector having at least one pin element and a cover, the cover including at least one aperture alignable with the at least one pin element.

6. The method of closing a surgical incision of claim 1, wherein placing the first connector in contact with tissue includes maintaining the second connector in contact with tissue and moving the deployment member relative to the second connector.

7. The method of closing a surgical incision of claim 1, wherein positioning the incision closure device includes the first connector having a first portion formed as a hollow body having an open end with a peripheral edge, and a second portion disposed over the open end.

8. The method of closing a surgical incision of claim 7, wherein positioning the incision closure device includes the first portion having a substantially half-spherical shape defining an interior chamber configured to receive one or more magnets therein.

9. The method of closing a surgical incision of claim 8, wherein positioning the incision closure device includes the first portion having at least one separating wall configured to separate the interior chamber of the first portion into a plurality of compartments configured to receive the one or more magnets therein.

10. The method of closing a surgical incision of claim 1, wherein positioning the incision closure device includes the second connector having a housing defining an interior chamber configured to receive one or more magnets therein.

11. The method of closing a surgical incision of claim 10, wherein positioning the incision closure device includes the housing having an opening formed therein configured to receive a portion of the deployment member therethrough.

12. The method of closing a surgical incision of claim 10, wherein positioning the incision closure device includes the housing further having a support member, the support member including a collar portion defining an opening configured to receive a portion of the deployment member therethrough.

13. The method of closing a surgical incision of claim 12, wherein positioning the incision closure device includes the support member further having a plurality of separating arms extending generally radially outward from the collar portion toward the housing.

14. The method of closing a surgical incision of claim 13, wherein positioning the incision closure device includes each separating arm of the plurality of separating arms having at least one non-magnetic material.

15. The method of closing a surgical incision of claim 1, wherein positioning the incision closure device includes the deployment member having at least one of a flexible material, a malleable material, or a shape memory material.

16. The method of closing a surgical incision of claim 1, wherein positioning the incision closure device includes the deployment member having a length and a substantially uniform diameter throughout the length of the deployment member.

* * * * *